United States Patent [19]

Weferling et al.

[11] Patent Number: 4,752,648

[45] Date of Patent: Jun. 21, 1988

[54] PROCESS FOR MAKING CHLOROPHOSPHINES AND THIOPHOSPHINIC ACID CHLORIDES, AND 9-CHLORO-9-THIOXO-9-PHOSPHABICY-CLONONANES

[76] Inventors: Norbert Weferling, Schaesbergstrasse 13, Hürth; Werner Klose, Grachtstrasse 14, Erftstadt, both of Fed. Rep. of Germany

[21] Appl. No.: 908,999

[22] Filed: Sep. 18, 1986

[30] Foreign Application Priority Data

Oct. 2, 1985 [DE] Fed. Rep. of Germany ....... 3535149

[51] Int. Cl.$^4$ .................. C07C 161/02; C07F 9/34; C07F 9/53
[52] U.S. Cl. ........................................ 558/10; 558/13; 560/301; 260/543 P
[58] Field of Search ...................... 260/543 P

[56] References Cited

U.S. PATENT DOCUMENTS

| | | | |
|---|---|---|---|
| 2,437,796 | 3/1948 | Walling | 260/543 P |
| 2,437,798 | 3/1948 | Walling | 260/543 P |
| 3,074,994 | 1/1963 | Grayson | 260/543 P |

OTHER PUBLICATIONS

Van Wazer, John R. *Phosphorus and Its Compounds,* vol. I (1958), Interscience Publ. at p. 192.
Kirk-Othmer Encyclopedia of Chemical Technology 2nd Ed. (vol. 15) at p. 303.

*Primary Examiner*—Donald B. Moyer
*Assistant Examiner*—L. Hendriksen

[57] ABSTRACT

Chlorophosphines or thiophosphinic acid chlorides of the general formulae $RPCl_2$, $R_2PCl$ or $R_2P(=S)Cl$ are made from feed materials selected from hydrogen-functional primary or secondary phosphines or secondary phosphine sulfides, where R stands for identical or different, linear or branched, substituted or unsubstituted alkyl radicals having from 1-16 carbon atoms, aryl radicals, aralkyl radicals or alkylaryl radicals having from 6-9 carbon atoms or cycloalkyl radicals having from 5-10 carbon atoms. To this end, the feed materials are reacted with phosphorus pentachloride, or with chlorine gas in the presence of phosphorus trichloride at temperatures within the range $-78°$ to $+145°$ C. It is possible for two radicals R to be linked together by one or two substituted or unsubstituted hydrocarbon chains having from 1-4 carbon atoms.

8 Claims, No Drawings

PROCESS FOR MAKING CHLOROPHOSPHINES AND THIOPHOSPHINIC ACID CHLORIDES, AND 9-CHLORO-9-THIOXO-9-PHOSPHABICYCLONONANES

This invention relates to a process for making chlorophosphines or thiophosphinic acid chlorides of the general formulae $RPCl_2$, $R_2PCl$ or $R_2P(=S)Cl$ from feed materials selected from hydrogen-functional primary or secondary phosphines or secondary phosphine sulfides, where R stands for identical or different, linear or branched, substituted or unsubstituted alkyl radicals having from 1-16 carbon atoms, aryl radicals, aralkyl radicals or alkylaryl radicals having from 6-9 carbon atoms or cycloalkyl radicals having from 5-10 carbon atoms.

A process of this kind has already been described in German Specification DE-A1 No. 32 35 787, wherein the feed materials are reacted with hexachloroethane at temperatures of 20°-180° C. As taught in this specification, it is possible for two radicals R to also constitute CH-bridge members of a bicyclic ring system containing a P-atom and, besides the two CH-bridge members, a further 4-6 carbon atoms. The use of hexachloroethane is however not unhazardous toxicologically and in addition rather expensive.

Attempts have already been made in the past to prepare primary and secondary chlorophosphines by subjecting corresponding organic phosphines to a chlorination reaction with chlorine (cf. U.S. Pat. Nos. 2,437,796 and 2,437,798). It has however turned out that these experiments were not reproducible, and preference has therefore been given to the use of phosgene as a chlorinating agent (cf. E. Steininger, Chem. Ber. 96 (1963), 3184–9, and U.S. Pat. No. 3,074,994 and GB-A No. 904 086).

The use of very toxic phosgene is however very hazardous and often leads to unsatisfactory results.

The process of this invention provides more particularly for the feed materials to be reacted with phosphorus pentachloride, or with chlorine gas in the presence of phosphorus trichloride, at temperatures within the range −78° C. to +145° C., and it also provides for two radicals R to be linked together by one or two substituted or unsubstituted hydrocarbon chains having from 1-4 carbon atoms.

Further preferred and optional features of the process of this invention provide:
(a) for the reaction with phosphorus pentachloride to be carried out at temperatures within the range 0° C.-111° C.;
(b) for the feed materials and chlorine gas to be introduced jointly in equivalent stoichiometric proportions into phosphorus trichloride at temperatures within the range −50° C. to 0° C.;
(c) for the reaction to be carried out in the presence of an inert solvent;
(d) for the solvent to be selected from linear or branched aliphatic hydrocarbons having more than 5 carbon atoms, methylcyclohexane or aromatic hydrocarbons;
(e) for toluene or a xylene to be used as the solvent.

The invention finally provides as a novel chemical substance an isomer mixture consisting of 9-chloro-9-thioxo-9-phosphabicyclo[3.3.1] and [4.2.1]nonanes of the formula

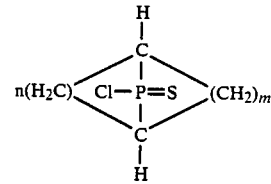

in which m=n=3 or m=2 and n=4.

These two novel compounds are typical of the special case where two radicals R are linked together by means of two hydrocarbon chains having from 1-4 carbon atoms.

As defined herein, it is possible for one or more hydrogen atoms present in the alkyl, aryl, aralkyl, alkylaryl or cycloalkyl radicals as well as in the hydrocarbon chains linking two radicals R together to be substituted. The useful substituents include atoms or atomic groupings which fail to undergo reaction with the chlorinating agent, e.g. halogenes (F—, Cl—, Br—, I—), pseudohalogenes (—SCN, —OCN), sulfo- (—SO₃H) or nitro groups (—NO₂).

Toluene (bp 110.6° C.) or a xylene (pb 138°-145° C.) should conveniently be used as the solvent; it is preferable for $PCl_5$ or $PCl_3$ to be dissolved in the solvent or to be used as a suspension, and for the feed material to undergo chlorination to be also dissolved in the solvent, and to be added gradually.

The reactions in this invention occur in accordance with the following equations

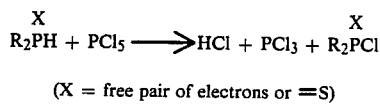

(X = free pair of electrons or =S)

or

In order to avoid side reactions, it is good practice to use $PCl_5$ in stoichiometric proportions. In the event of $PCl_5$ being replaced by its feed materials $PCl_3$ and $Cl_2$, it is possible to use $PCl_3$ in substoichiometric proportions, quasi as a catalyst. $PCl_3$ is invariably obtained upon the use of $PCl_5$; due to its low boiling point of 75.9° C., it is however very easy to separate from the chlorinated organophosphorus compound and easy to reconvert to $PCl_5$, if desired in a separate reaction with elementary chlorine.

The commonly observed smooth formation of the chloro-functional P-compounds of this invention would not have been expected from the onset as the primary and secondary phosphine feed materials are definitely able to undergo further reaction also with phosphonous acid chlorides (dichlorophosphines) or phosphinic acid chlorides (chlorophosphines) as the reaction products and give diphosphines, HCl being split off. In addition, it is possible for $PCl_3$ to undergo an exothermal reaction with phosphines (feed material) to give insoluble, presumably polymeric red-orange solid matter. Finally, stable acid/base-addition products of primary or secondary phosphine and the couple product HCl could indeed be expected to form.

The reactions proceed especially smoothly with good to very good yields where phosphines of low basicity are the feed materials. Merely during the reaction of the relatively strongly basic di-n-dibutylphosphine with PCl$_5$ was it possible to observe the formation of a stable phosphonium salt ([Bu$_2$P$^\oplus$Cl$_2$]Cl$^\ominus$) which strongly reduced the yield of the chlorophosphine targeted (cf. Example 5).

The process of this invention offers the advantage of being comparably reliable toxicologically. PCl$_5$ is an inexpensive chlorinating agent easy to handle.

The compounds PCl$_3$ and HCl which are obtained as byproducts can be reput to suitable uses. The compounds made by this invention especially the isomer mixture of 9-chloro-9-thioxo-9-phosphabicyclo[3.3.1] and [4.2.1]nonanes are suitable intermediates for synthesizing pharmaceutical preparations and plant protecting agents.

EXAMPLE 1

(preparation of monocyclohexyldichlorophosphine)

319 g (1.05 mol) of a 38 wgt % monocyclohexylphosphine solution in toluene was added dropwise at 25° C. to a suspension of 436 g PCl$_5$ (2.1 mol) in 1 liter toluene. After the strongly exothermal reaction was complete, the reaction mixture was filtered using a reverse frit. 5 g orange colored solid matter remained behind. The clear solution ($^{31}$P-NMR; $\delta$ P: 195 ppm, C$_6$H$_{11}$PCl$_2$, 95 mol %) was distilled under vacuum.

bp 50° C./0.1 mbar; yield 170 g (88% of theoretical).

EXAMPLE 2

(preparation of secondary butyldichlorophosphine)

A solution of 70 g (0.78 mol) mono.sec.-butylphosphine in 70 g toluene was dropped at 25° C. into a suspension of 324 g (1.56 mol) PCl$_5$ in 500 g toluene. An exothermal reaction took place with evolution of HCl. The phosphine was metered so that the maximum temperature was 50° C. After all had been dropped in, the whole was stirred at 80° C. until HCl ceased to be evolved. The reaction mixture was clear and homogeneous. The low boilers were removed at room temperature under 30 mbar. $^{31}$P-NMR: $\delta$ P=201 ppm, sec.-C$_4$H$_9$PCl$_2$, 87 mol %; $\delta$ P=57.1 ppm, sec.-C$_4$H$_9$Cl$_2$, 3 mol %.

The residue was distilled under vacuum.

pb. 70° C./53 mbar; yield 50 g (40% of the theoretical)

EXAMPLE 3

(preparation of phenyldichlorophosphine)

38.5 g (0.34 mol) phenylphosphine dissolved in 40 ml toluene was added at 25° C. to a suspension of 160 g PCl$_5$ (0.77 mol) in 500 ml toluene. After the exothermal reaction had subsided, the whole was heated to 70° C. until gas ceased to be evolved. The low boilers were removed under vacuum. The crude product yield was 67 g; $^{31}$P-NMR: $\delta$ P=161 ppm, C$_6$H$_5$PCl$_2$, 94.4 mol%. The residue was distilled under vacuum. bp 98° C./17 mbar; yield: 50.6 g (81% of the theoretical).

EXAMPLE 4

(preparation of dicyclohexylchlorophosphine)

A solution of 19 g (0.1 mol) dicyclohexylphosphine in 50 ml toluene was dropped into a suspension of 21 g (0.1 mol) PCl$_5$ in 100 ml toluene. The reaction temperature was maintained at less than 30° C. After all had been dropped in, the whole was boiled for 1 hour under reflux. A slight precipitate was removed by means of a reverse frit and the reaction mixture was freed from all low boilers at 60° C. under 0.1 mbar. Yield: 23.3 g; $^{31}$P-NMR: $\delta$ P=126 ppm, (c-C$_6$H$_{11}$)$_2$PCl, 96 mol %; $\delta$ P=54 ppm, (c-C$_6$H$_{11}$)$_2$P(O)Cl, 3.7 mol %.

EXAMPLE 5

(preparation of di-n-butylchlorophosphine)

148 g (1 mol) di-n-butylphosphine was dropped at a maximum reaction temperature of 30° C. into a suspension of 232 g (1.1 mol) PCl$_5$ in 500 ml toluene. HCl and PCl$_3$ formed during the reaction were removed under a vacuum of 130 mbar and condensed in a cooling trap. After the reaction was complete, the reaction mixture was found to comprise two liquid phases. The upper phase contained PCl$_3$ in toluene. The bulk quantity of chlorophosphine was in the lower phase ($^{31}$P-NMR). It was worked up distillatively and 101 g product was obtained (55% of the theoretical). bp 92° C./16 mbar.

EXAMPLE 6

(preparation of 9-chloro-9-phosphabicyclo[3.3.1] and [4.2.1]nonanes (isomer mixture)

A solution of 115 g (0.8 mol) 9H-9-phosphabicyclo[3.3.1] and [4.2.1]nonanes in 500 ml toluene was dropped at room temperature into a mixture of 167 g (0.8 mol) PCl$_5$ and 900 ml toluene. After the exothermal reaction was complete, the whole was allowed to undergo post-reaction over a period of 2 hours. P-NMR spectroscopy on a crude product specimen indicated that the reaction was indeed complete and that merely the two isomeric chlorophosphines had been formed. After the removal of a minor quantity of an orange-colored precipitate, the mixture was freed from all low boilers under vacuum. Yield: 119 g (83.5% of the theoretical).

EXAMPLE 7

(preparation of 9-chloro-9-thioxo-9-phosphabicyclo[3.3.1] and [4.2.1]nonanes (isomer mixture)

162 g (0.9 mol) 9H-9-thioxo-9-phosphabicyclo[3.3.1] and [4.2.1]nonanes (isomer mixture) and 194 g (0.9 mol) PCl$_5$ were mixed with 500 ml toluene at room temperature in the absence of any noticeable reaction taking place. On heating the mixture, the expected dehydrochlorination was observed from about 50° C. upward. The whole was heated under reflux until gas ceased to be evolved. A minor quantity of precipitated matter was removed and all of the low boilers were removed under vacuum. The solid residue could be recrystallized from toluene. Yield: 120 g (62% of the theoretical). $^{31}$P-NMR: $\delta$ P=122.3 ppm, 105.7 ppm.

Analytical data: P calc. 14.8%; C calc. 46.5%; H calc. 7.2%. P found 14.8%; C found 46.7%; H found 6.8%.

EXAMPLE 8

(preparation of dicyclohexylthiophosphinic acid chloride)

A solution of 23 g (0.1 mol) dicyclohexylphosphine sulfide in 50 ml toluene was dropped into a suspension of 21 g (0.1 mol) PCl$_5$ in 50 ml toluene. The reaction was exothermal and reached a maximum temperature of 35° C. After 4 hours, the low boilers were removed from the clear yellowish solution under vacuum. Yield: 24.3 g (91.5% of the theoretical). $^{31}$P-NMR: δ P=119.3 ppm.

EXAMPLE 9

(preparation of dicyclohexylchlorophosphine with PCl$_3$/Cl$_2$)

70 g (0.5 mol) PCl$_3$ was dissolved in 200 ml toluene and the solution was cooled to $-30°$ C. Next, 100 g (0.5 mol) dicyclohexylphosphine and the stoichiometric quantity of chlorine gas were introduced jointly within 1 hour. The maximum temperature was $-10°$ C. The slightly yellowish clear solution was decanted from minor quantities of a red-brown solid precipitate. A specimen was subjected to $^{31}$P-NMR-spectroscopy; the feed compound was found to have been completely reacted. Apart from PCl$_3$, two phosphorus-containing compounds were determined: δ P=126 ppm, (c-C$_6$H$_{11}$)$_2$PCl, 98 mol %; δ P=139.7 ppm, (c-C$_6$H$_{11}$)$_2$PCl$_2$$^⊕$Cl$^⊖$, 2 mol %.

120 g residue (117 g (c-C$_6$H$_{11}$)$_2$PCl would correspond to a 100% yield) was obtained after all of the readily volatile compounds had been removed.

We claim:

1. A process for making chlorophosphines or thiophosphinic acid chlorides of the general formulae RPCl$_2$, R$_2$PCl or R$_2$P(=S)Cl from feed materials selected from primary or secondary phosphines or secondary phosphine sulfides, where R stands for identical or different, linear or branched, unsubstituted or halogen-, cyanate-, thiocyanato-, sulfo- or nitro-substituted alkyl radicals having from 1–16 carbon atoms, aryl radicals, aralkyl radicals or alkylaryl radicals having from 6–9 carbon atoms or cycloalkyl radicals having from 5–10 carbon atoms, which comprises: reacting the feed materials with phosphorus pentachloride, or with chlorine gas in the presence of phosphorus trichloride at temperatures within the range $-78°$ to $+145°$ C.

2. A process as claimed in claim 1, wherein two radicals R are linked together by one or two unsubstituted or halogen-, cyanato-, thiocyanato-, sulfo- or nitro-substituted hydrocarbon chains having from 1–4 carbon atoms.

3. A process as claimed in claim 1, wherein the reaction with phosphorus pentachloride is carried out at temperatures within the range 0°–111° C.

4. A process as claimed in claim 1, wherein the feed materials and chlorine gas are introduced jointly in equivalent stoichiometric proportions into phosphorus trichloride at temperatures within the range $-50°$ to 0° C.

5. A process as claimed in claim 1, wherein the reaction is carried out in the presence of an inert solvent.

6. A process as claimed in claim 5, wherein the solvent is selected from linear or branched aliphatic hydrocarbons having more than 5 carbon atoms, methylcyclohexane or aromatic hydrocarbons.

7. A process as claimed in claim 5, wherein the solvent used is toluene or a xylene.

8. Isomer mixture consisting of 9-chloro-9-thioxo-9-phosphabicyclo[3.3.1] and [4.2.1]nonanes.

* * * * *